United States Patent [19]

Cornils et al.

[11] Patent Number: 4,533,755

[45] Date of Patent: Aug. 6, 1985

[54] PROCESS FOR THE HYDROFORMYLATION OF OLEFINS

[75] Inventors: Boy Cornils, Dinslaken; Josef Hibbel, Oberhausen; Gunther Kessen, Oberhausen; Werner Konkol, Oberhausen; Bernhard Lieder, Bottrop; Ernst Wiebus, Oberhausen; Heinz Kalbfell, Schermbeck; Hanswilhelm Bach, Duisburg, all of Fed. Rep. of Germany

[73] Assignee: Ruhrchemie Aktiengesellschaft, Oberhausen, Fed. Rep. of Germany

[21] Appl. No.: 558,788

[22] Filed: Dec. 7, 1983

[30] Foreign Application Priority Data

Dec. 11, 1982 [DE] Fed. Rep. of Germany ....... 3245883

[51] Int. Cl.$^3$ ..................... C07C 45/50; C07C 27/20
[52] U.S. Cl. ..................... 568/454; 568/909

[58] Field of Search .............. 568/451, 454, 909

[56] References Cited

U.S. PATENT DOCUMENTS

| | | | |
|---|---|---|---|
| 4,242,283 | 12/1980 | Hibbel et al. | 568/451 |
| 4,258,215 | 3/1981 | Dawes | 568/454 |
| 4,267,383 | 5/1981 | Booth | 568/454 |

FOREIGN PATENT DOCUMENTS 3102281  1/1982  Fed. Rep. of Germany ...... 568/451

*Primary Examiner*—Werren B. Lone
*Attorney, Agent, or Firm*—Jordan B. Bierman

[57] ABSTRACT

A process for the hydroformylation of olefins having 2 to 5 carbon atoms using rhodium catalysts in a low pressure process, wherein the waste gas from the low pressure plant containing the olefin is compressed and used in a high pressure plant.

9 Claims, No Drawings

PROCESS FOR THE HYDROFORMYLATION OF OLEFINS

This application claims the priority of German application No. P 32 45 883.5, filed Dec. 11, 1982.

The invention relates to an especially useful variant of the oxo synthesis which is conducted in two stages. According to this invention, the waste gases from oxo plants, which are operated at low reaction pressures and which still contain considerable amounts of unreacted olefin, are collected in a suitable manner and subsequently reacted in high pressure oxo plants.

In addition to laboratory methods, there are three commercial processes for the hydroformylation of olefins. In the high pressure (HP) process, starting olefins are reacted with synthesis gas at pressures of 100 to 350 bar and temperatures of 120° to 180° C. Particular temperatures and pressures are chosen depending on the number of carbon atoms in the olefin and the desired reaction product—aldehydes or alcohols. The active catalysts of the reaction are hydridocobalt tetracarbonyls which can be introduced as such or can be formed during the reaction from suitable cobalt precursors. These high pressure processes are generally characterized by high olefin conversions so that costly measures for the recovery and recycling of olefins are unnecessary. The waste gas of the high pressure reaction, therefore, contains principally the corresponding saturated hydrocarbon and synthesis gas in addition to small amounts of the starting olefin. Treatment of the HP waste gas in an additional high pressure stage is not economically viable because of the almost complete initial conversion. Also, the waste gas, containing unreacted propylene in small concentrations, would have to be recompressed.

In the medium pressure (MP) process, cobalt catalysts modified with phosphines are used. The low reaction pressure of 50 to 100 bars leads, among other things, to a fall in olefin conversion. The phosphine-cobalt catalysts have a strong hydrogenative effect under the reaction conditions; therefore, the unreacted olefin in the product is usually substantially contaminated with corresponding saturated hydrocarbons. Since the olefin can only be reused if a costly olefin—saturated hydrocarbon separation is carried out, the olefin recovery and recycling are dispensed with in most cases.

Finally, in the low pressure (LP) oxo process, phosphine-rhodium catalysts are used which permit hydroformylation at temperatures of 60° to 150° C. and pressures of 10 to 80 bar. The main advantage of the low pressure process is the high selectivity of the hydroformylation reaction.

The disadvantage of all low pressure processes is that the low reaction temperatures permit only a limited olefin conversion using technical grade propylene. Therefore, for economic reasons, the starting olefin must be recovered and recycled.

On the other hand, the rhodium catalysts modified by ligands are advantageous, since they have a much smaller tendency to hydrogenate the starting olefin than do the cobalt-phosphine catalysts. Thus, the formation of saturated hydrocarbons as a result of hydrogenation is less than in the MP process. However, even in the LP-oxo synthesis with continuous recovery and continuous recycling of the unreacted starting olefin from each reactor run, saturated hydrocarbon/olefin separations are necessary. If such a separation is dispensed with, a disproportionately large amount of olefin is lost along with the saturated compound which is of no use in the oxo stage.

The ideal conversion of the residual propylene in downstream low pressure plants would require the installation of an uneconomic cascade circuit. According to a method described in the DOS No. 31 02 281, the waste gases containing propylene from existing HP processes are fed into an LP plant. Therefore, the conventional HP-oxo plants are supplemented or replaced step-by-step by LP processes. A disadvantage of this combined process is that all the olefins, even that which is only to be reacted in the low pressure stage, must initially be compressed. Moreover, an LP plant for the utilization of residual propylene from the HP plants is very costly.

The present invention avoids the aforementioned disadvantages. It comprises the hydroformylation of olefins having 2 to 5 carbon atoms using rhodium catalysts in a low pressure process followed by high pressure hydroformylation using cobalt catalysts. Here the waste gas from the LP plant containing unreacted olefin is compressed and used in a high pressure plant.

Surprisingly, the practicability of the method according to the invention is not affected by the fact that the waste gas from the low pressure process usually contains traces of phosphines which act as a poison to the cobalt catalyst in the high pressure stage. It has been discovered that, despite this phosphine content, the waste gas can be used in the HP plant (high pressure stage) of the combined process with high conversion and without damage to the catalyst. Furthermore, the completeness of the reaction is unexpectedly not affected by the fact that the waste gas of the low pressure plant contains a relatively large amount of hydrogen which should lead to a reduction in the aldehyde yield in the high pressure stage. Finally, in the process according to the invention, it is not necessary to use ultra pure olefin in the low pressure stage. It is sufficient to use standard commercial olefins containing some saturated hydrocarbons. In the case of propylene, for example, about 5% propane is present. The saturated compounds can be expelled from the process together with the waste gas from the high pressure stage.

The reactions in the LP and HP stages of the process are carried out according to known methods. The LP stage is operated at a pressure of 10 to 80 bar and a temperature of 60° to 150° C. Rhodium finds application as a catalyst together with organic phosphines. The rhodium is used as the metal or a compound thereof; e.g. as rhodium chloride, rhodium oxide, or rhodium acetate; in concentrations of 200 ppm to 800 ppm. Aromatic phosphines such as triphenylphosphine have proved to be particularly suitable as the organic phosphine. They can also be a component of the reaction medium either separate from, or together with, the high-boiling by-products of the synthesis.

The atom or mole ratio of rhodium to phosphine can be 1:2,000 to 1:30, depending on the reaction medium. When water-soluble phosphines are used, water can also be used as the reaction medium. Phosphines whose organic groups have been carboxylated or sulfonated are soluble in water.

The waste gas leaving the low pressure reactor generally has a composition in the following range (all percents are by volume):

25–40% propylene, 6–20% propane, 20–40% hydrogen and 20–40% carbon monoxide. Without further intermediate treatment, it is compressed to a pressure of 100 to 350 bar and reacted at temperatures of 120° to 180° C. Cobalt is used as a catalyst in its metallic form or as a compound thereof. The resulting reaction product is the medium for the reaction. The pressure is released, and the cobalt dissolved in the reaction product is removed. Thus, a waste gas is formed with the following composition using the standard technical processes (again, all percents are by volume):

1–2% propylene, 5–15% propane, 25–40% hydrogen and 45–55% carbon monoxide.

EXAMPLE 1

Reaction of propylene according to the HP process (comparison)

In a high pressure test reactor, standard technical propylene with a propane content of 5% is reacted with synthesis gas ($CO:H_2 = 1:1$) at 150° C. and a pressure of 260 bars. The throughput is 1 liter propylene/liter reactor volume, and the Co concentration is 0.5 weight-%, based on the reactor feed. With 98% conversion, based on the propylene feed, a reaction product with the following composition is obtained:

| | |
|---|---|
| $C_4$-aldehyde = | 84.2% |
| $C_4$-alcohols = | 2.9% |
| $C_4$-methylesters = | 5.1% |
| thick oil residue = | 7.8% |
| n/i ratio = | 75:25 |

This demonstrates that, 115.0 kg of n-$C_4$ value products are formed per 100 kg propylene (100%) taking into consideration a propane formation of 1%.

EXAMPLE 2

Reaction of propylene according to the LP process (comparison)

In a test reactor, standard commercial propylene with a propane content of 5% is reacted with synthesis gas ($CO:H_2 = 1:1$) at 120° C. and a pressure of 20 bars. The throughput is 0.2 liter propylene/liter reactor volume, and the rhodium concentration is 400 ppm, based on the reactor feed. With 87% conversion, based on the propylene feed, a reaction product with the following composition is obtained:

| | |
|---|---|
| $C_4$-aldehyde = | 98.8% |
| $C_4$-alcohols = | 0.5% |
| $C_4$-methylesters = | 0.1% |
| thick oil residue = | 0.6% |
| n/i ratio = | 90:10 |

Taking into consideration a propane formation of 0.2%, 133.0 kg n-$C_4$ value products are formed per 100 kg propylene (100%).

The quantity of gas necessary to expel the propane is 29.4 $Nm^3$/100 kg propylene with a propylene content of 23.4% and a propane content of 9.2%; the rest is $H_2$ and CO in a volume ratio of about 1:1.

EXAMPLE 3

Conversion of the LP process waste gas by the HP process

Waste gas from the LP process of Example 2 containing propylene is compressed and hydroformylated according to the HP process under the conditions of Example 1. With 96.7% conversion based on the amount of propylene starting material, hydroformylation takes place with even better selectivity than with fresh propylene. This is probably due to the diluent effect of the propane.

With a composition of the reaction product of

| | |
|---|---|
| $C_4$-aldehyde = | 85.6% |
| $C_4$-alcohols = | 2.9% |
| $C_4$-methylesters = | 4.5% |
| thick oil residue = | 7.0% |
| n/i-ratio = | 76:24, | the yield of n-$C_4$ value products is 115.2 per 100 kg of starting propylene, a propane formation of 1% being taken into consideration.

Based on a hydroformylation feed of 29.4 $Nm^3$ waste gas from the LP stage with a propylene content of 23.4 vol. % = 12.8 kg, a total yield of n-$C_4$ value products, amounting to 147.7 kg per 100 kg propylene, is obtained from the test hydroformylations according to Examples 2 and 3. This yield is thus 14.7 kg/100 kg. olefin more than the yield obtained from LP-hydroformylation without downstream conversion of the waste gas containing propylene in a high pressure reactor.

What we claim is:

1. A method for the hydroformylation of an olefin having 2 to 5 carbon atoms comprising
    (a) subjecting said olefin to a low pressure hydroformylation reaction with synthesis gas in the presence of a water-soluble phosphine-rhodium catalyst to yield a first product and a waste gas, said waste gas containing an unreacted portion of said olefin,
    (b) recovering and compressing said waste gas, and
    (c) subjecting the compressed waste gas to a high pressure hydroformylation reaction in the presence of a cobalt catalyst.

2. The method of claim 1 wherein said low pressure process is conducted from about 10 to about 80 bars and from about 60° to about 150° C.

3. The method of claim 1 wherein said high pressure process is conducted from about 100 to about 350 bars and from about 120° to about 180° C.

4. The method of claim 1 wherein said rhodium catalyst further comprises an organic phosphine.

5. The method of claim 1 wherein said rhodium catalyst comprises a rhodium component selected from rhodium metal, rhodium chloride, rhodium oxide, and rhodium acetate.

6. The method of claim 1 wherein said rhodium catalyst comprises a rhodium ion portion in an amount of 200 to 800 ppm based upon said rhodium catalyst.

7. The method of claim 4 wherein said rhodium and said phosphine are present in a ratio of rhodium to phosphine of 1:2000 to 1:30.

8. The method of claim 4 wherein said phosphine is triphenyl phosphine.

9. The method of claim 1 wherein said first olefins contain up to about 5% saturated hydrocarbons based on said first olefins.

* * * * *